US011553850B2

(12) United States Patent
Lee et al.

(10) Patent No.: US 11,553,850 B2
(45) Date of Patent: Jan. 17, 2023

(54) ELECTRONIC DEVICE AND METHOD FOR IDENTIFYING OCCURRENCE OF HYPOTENSION

(71) Applicant: Samsung Electronics Co., Ltd., Suwon-si (KR)

(72) Inventors: Hongji Lee, Suwon-si (KR); Jooman Han, Suwon-si (KR); Jeongmin Park, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 132 days.

(21) Appl. No.: 16/673,086

(22) Filed: Nov. 4, 2019

(65) Prior Publication Data

US 2020/0138308 A1 May 7, 2020

(30) Foreign Application Priority Data

Nov. 6, 2018 (KR) ........................ 10-2018-0135160

(51) Int. Cl.
*A61B 5/024* (2006.01)
*A61B 5/1455* (2006.01)
*A61B 5/026* (2006.01)

(52) U.S. Cl.
CPC ........ *A61B 5/02427* (2013.01); *A61B 5/0261* (2013.01); *A61B 5/14552* (2013.01)

(58) Field of Classification Search
CPC ............ A61B 5/02427; A61B 5/14552; A61B 5/0261; A61B 5/486; A61B 5/1116;
(Continued)

(56) References Cited

U.S. PATENT DOCUMENTS 8,923,941 B2 12/2014 Leboeuf et al.
2013/0296723 A1 11/2013 Cho et al.
(Continued)

FOREIGN PATENT DOCUMENTS

EP 2 519 277 A1 11/2012
JP 2017136240 A 8/2017
(Continued)

OTHER PUBLICATIONS

Sannino et al.; Blood Pressure Drop Prediction by using HRV Measurements in Orthostatic Hypotensio; Sep. 7, 2015.
(Continued)

*Primary Examiner* — Allen Porter
*Assistant Examiner* — Abid A Mustansir
(74) *Attorney, Agent, or Firm* — Jefferson IP Law, LLP

(57) ABSTRACT

An electronic device for identifying occurrence of hypotension and a method therefor are provided. The electronic device includes a housing, a user interface, a photoplethysmogram (PPG) sensor exposed through at least part of the housing, a motion sensor disposed in the housing, at least one processor operatively coupled with the user interface, the PPG sensor, and the motion sensor, and a memory operatively coupled with the at least one processor. The memory may store instructions which, when executed by the at least one processor, cause the at least one processor to, based on first data from the motion sensor indicating a change of a selected pattern, identify a blood pressure value based at least in part on second data from the PPG sensor, and based on the identified blood pressure value being lower than a first threshold, provide a notification through the user interface.

12 Claims, 10 Drawing Sheets

(58) Field of Classification Search
CPC ... A61B 5/7275; A61B 5/02416; A61B 5/681; A61B 5/02108
See application file for complete search history.

(56) References Cited

U.S. PATENT DOCUMENTS

| | | | |
|---|---|---|---|
| 2016/0029904 A1* | 2/2016 | Quinn | A61B 5/11 600/499 |
| 2016/0270708 A1* | 9/2016 | Tateda | A61B 5/742 |
| 2017/0042485 A1 | 2/2017 | Chung et al. | |
| 2017/0172431 A1* | 6/2017 | Kim | A61B 5/02125 |
| 2017/0181649 A1* | 6/2017 | Carter | A61B 5/02416 |
| 2017/0209055 A1* | 7/2017 | Pantelopoulos | A61B 5/7203 |
| 2018/0008205 A1 | 1/2018 | Al Hatib et al. | |
| 2018/0206735 A1 | 7/2018 | Holz et al. | |
| 2019/0150755 A1 | 5/2019 | Nakajima et al. | |
| 2021/0059542 A1* | 3/2021 | Gopalakrishnan | G06Q 50/01 |

FOREIGN PATENT DOCUMENTS

| | | |
|---|---|---|
| KR | 10-2013-0123597 A | 11/2013 |
| KR | 10-2018-0024266 A | 3/2018 |
| KR | 10-2020-0100936 A | 8/2020 |
| WO | 2011/080190 A1 | 7/2011 |
| WO | 2017/179694 A1 | 10/2017 |
| WO | 2018/017425 A1 | 1/2018 |

OTHER PUBLICATIONS

Juraschek et al.; Association of History of Dizziness and Long-term Adverse Outcomes With Early vs Later Orthostatic Hypotension Assessment Times in Middle-aged Adults; Downloaded From: https://jamanetwork.com/ on Jul. 24, 2017.
International Search Report dated Feb. 20, 2020, issued in an International Application No. PCT/KR2019/014847.
European Search Report dated Oct. 25, 2021; European Appln. No. 19882100.1-1113 / 3856018 PCT/KR2019014847.

* cited by examiner

ELECTRONIC DEVICE AND METHOD FOR IDENTIFYING OCCURRENCE OF HYPOTENSION

CROSS-REFERENCE TO RELATED APPLICATION(S)

This application is based on and claims priority under 35 U.S.C. § 119(a) of a Korean patent application number 10-2018-0135160, filed on Nov. 6, 2018, in the Korean Intellectual Property Office, the disclosure of which is incorporated by reference herein in its entirety.

BACKGROUND

1. Field

The disclosure relates to a method and an electronic device for identifying occurrence of hypotension.

2. Description of Related Art

In recent, a technique for monitoring a biometric signal of a user using an electronic device such as a smartphone and a wearable device is developing. Specifically, various sensing techniques and services are growing for continual monitoring such as blood sugar and hypertension. The disclosure relates to sensing and predicting the biometric signal of the user.

The above information is presented as background information only to assist with an understanding of the disclosure. No determination has been made, and no assertion is made, as to whether any of the above might be applicable as prior art with regard to the disclosure.

SUMMARY

Compared to a service for hypertensive patients, a service for hypotension is insufficient. In this regard, what is demanded is a service for monitoring user's hypotension.

Aspects of the disclosure are to address at least the above-mentioned problems and/or disadvantages and to provide at least the advantages described below. Accordingly, an aspect of the disclosure is to provide an electronic device and a method for predicting or determining hypotension occurrence of a user of an electronic device.

Additional aspects will be set forth in part in the description which follows and, in part, will be apparent from the description, or may be learned by practice of the presented embodiments.

In accordance with an aspect of the disclosure, an electronic device is provided. The electronic device includes a housing, a user interface, a photoplethysmogram (PPG) sensor exposed through at least part of the housing, a motion sensor disposed in the housing, at least one processor operatively coupled with the user interface, the PPG sensor, and the motion sensor, and a memory operatively coupled with the at least one processor, wherein the memory may store instructions which, when executed by the at least one processor, cause the at least one processor to, based on first data from the motion sensor indicating a change of a selected pattern, identify a blood pressure value based at least in part on second data from the PPG sensor, and based on the identified blood pressure value being lower than a first threshold, provide a notification through the user interface.

In accordance with another aspect of the disclosure, an operating method of an electronic device is provided. The operating method includes, based on first data from a motion sensor of the electronic device indicating a change of a selected pattern, identifying a blood pressure value based at least in part on a second data from a PPG sensor of the electronic device, and based on the identified blood pressure value being lower than a first threshold, providing a notification through a user interface of the electronic device.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

Throughout the drawings, like reference numerals will be understood to refer to like parts, components and structures.

DETAILED DESCRIPTION

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Figure 1:
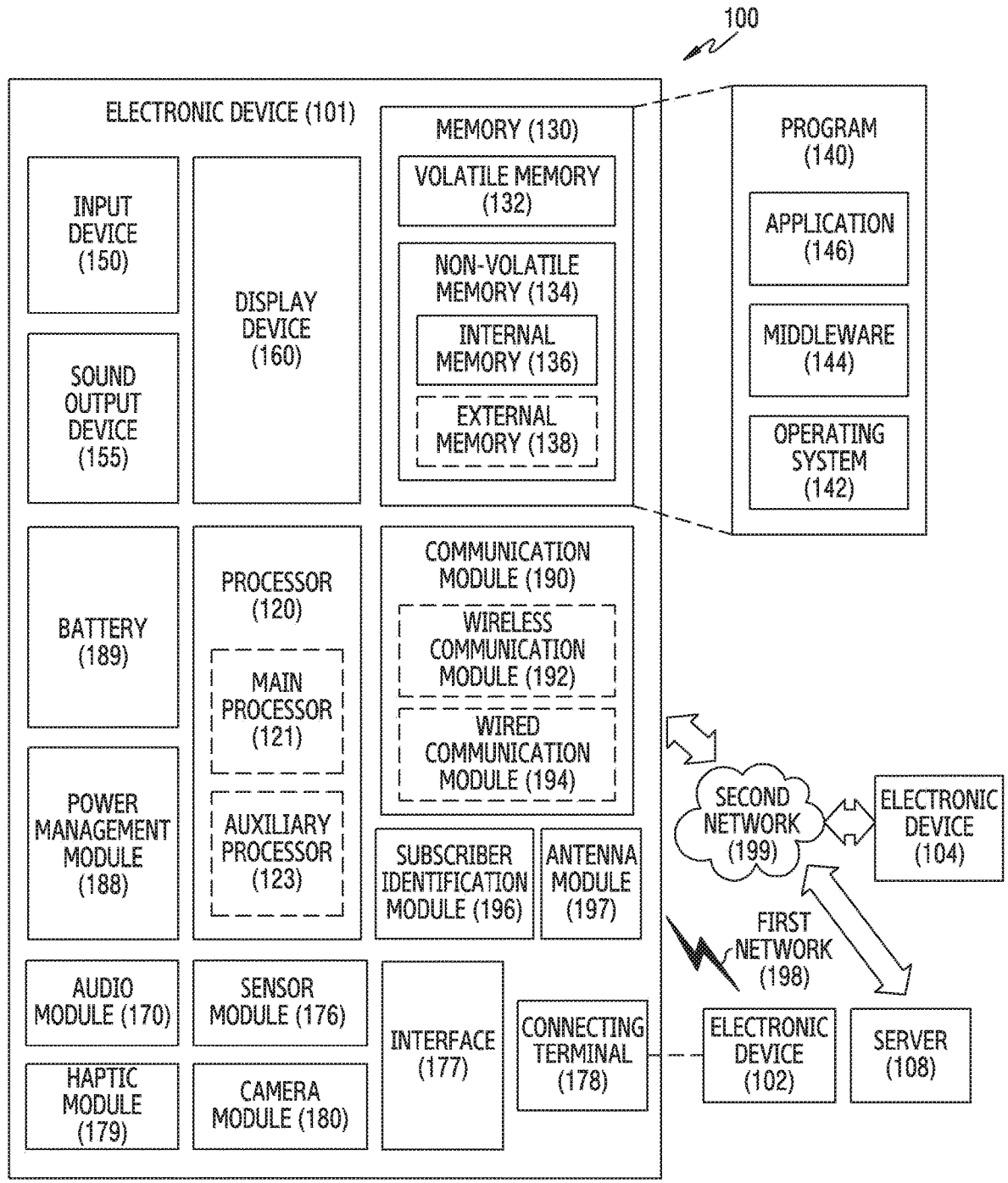
FIG. 1 is a block diagram of an electronic device in a network environment according to an embodiment of the disclosure.

FIG. 1 is a block diagram illustrating an electronic device (101) in a network environment (100) according to an embodiment of the disclosure.

Referring to FIG. 1, the electronic device (101) in the network environment (100) may communicate with an electronic device (102) via a first network (198) (e.g., a short-range wireless communication network), or an electronic device (104) or a server (108) via a second network (199) (e.g., a long-range wireless communication network). According to an embodiment, the electronic device (101) may communicate with the electronic device (104) via the server (108). According to an embodiment, the electronic device (101) may include a processor (120), memory (130), an input device (150), a sound output device (155), a display device (160), an audio module (170), a sensor module (176), an interface (177), a haptic module (179), a camera module (180), a power management module (188), a battery (189), a communication module (190) (e.g., a transceiver), a subscriber identification module(SIM) (196), or an antenna module (197). In some embodiments, at least one (e.g., the display device (160) or the camera module (180)) of the components may be omitted from the electronic device (101), or one or more other components may be added in the electronic device (101). In some embodiments, some of the components may be implemented as single integrated circuitry. For example, the sensor module (176) (e.g., a fingerprint sensor, an iris sensor, or an illuminance sensor) may be implemented as embedded in the display device (160) (e.g., a display).

The processor (120) may execute, for example, software (e.g., a program (140)) to control at least one other component (e.g., a hardware or software component) of the electronic device (101) coupled with the processor (120), and may perform various data processing or computation. According to one embodiment, as at least part of the data processing or computation, the processor (120) may load a command or data received from another component (e.g., the sensor module (176) or the communication module (190)) in volatile memory (132), process the command or the data stored in the volatile memory (132), and store resulting data in non-volatile memory (134). According to an embodiment, the processor (120) may include a main processor (121) (e.g., a central processing unit (CPU) or an application processor (AP)), and an auxiliary processor (123) (e.g., a graphics processing unit (GPU), an image signal processor (ISP), a sensor hub processor, or a communication processor (CP)) that is operable independently from, or in conjunction with, the main processor (121). Additionally or alternatively, the auxiliary processor (123) may be adapted to consume less power than the main processor (121), or to be specific to a specified function. The auxiliary processor (123) may be implemented as separate from, or as part of the main processor (121).

The auxiliary processor (123) may control at least some of functions or states related to at least one component (e.g., the display device (160), the sensor module (176), or the communication module (190)) among the components of the electronic device (101), instead of the main processor (121) while the main processor (121) is in an inactive (e.g., sleep) state, or together with the main processor (121) while the main processor (121) is in an active state (e.g., executing an application). According to an embodiment, the auxiliary processor (123) (e.g., an image signal processor or a communication processor) may be implemented as part of another component (e.g., the camera module (180) or the communication module (190)) functionally related to the auxiliary processor (123).

The memory (130) may store various data used by at least one component (e.g., the processor (120) or the sensor module (176)) of the electronic device (101). The various data may include, for example, software (e.g., the program (140)) and input data or output data for a command related thereto. The memory (130) may include the volatile memory (132) or the non-volatile memory (134).

The program (140) may be stored in the memory (130) as software, and may include, for example, an operating system (OS) (142), middleware (144), or an application (146).

The input device (150) may receive a command or data to be used by the other component (e.g., the processor (120)) of the electronic device (101), from the outside (e.g., a user) of the electronic device (101). The input device (150) may include, for example, a microphone, a mouse, a keyboard, or a digital pen (e.g., a stylus pen).

The sound output device (155) may output sound signals to the outside of the electronic device (101). The sound output device (155) may include, for example, a speaker or a receiver. The speaker may be used for general purposes, such as playing multimedia or playing record, and the receiver may be used for incoming calls. According to an embodiment, the receiver may be implemented as separate from, or as part of the speaker.

The display device (160) may visually provide information to the outside (e.g., a user) of the electronic device (101). The display device (160) may include, for example, a display, a hologram device, or a projector and control circuitry to control a corresponding one of the display, hologram device, and projector. According to an embodiment, the display device (160) may include touch circuitry adapted to detect a touch, or sensor circuitry (e.g., a pressure sensor) adapted to measure the intensity of force incurred by the touch.

The audio module (170) may convert a sound into an electrical signal and vice versa. According to an embodiment, the audio module (170) may obtain the sound via the input device (150), or output the sound via the sound output device (155) or a headphone of an external electronic device (e.g., an electronic device (102)) directly (e.g., wiredly) or wirelessly coupled with the electronic device (101).

The sensor module (176) may detect an operational state (e.g., power or temperature) of the electronic device (101) or an environmental state (e.g., a state of a user) external to the electronic device (101), and then generate an electrical signal or data value corresponding to the detected state. According to an embodiment, the sensor module (176) may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface (177) may support one or more specified protocols to be used for the electronic device (101) to be coupled with the external electronic device (e.g., the electronic device (102)) directly (e.g., wiredly) or wirelessly. According to an embodiment, the interface (177) may include, for example, a high definition multimedia interface (HDMI), a universal serial bus (USB) interface, a secure digital (SD) card interface, or an audio interface.

A connecting terminal (178) may include a connector via which the electronic device (101) may be physically connected with the external electronic device (e.g., the electronic device (102)). According to an embodiment, the connecting terminal (178) may include, for example, a HDMI connector, a USB connector, a SD card connector, or an audio connector (e.g., a headphone connector).

The haptic module (179) may convert an electrical signal into a mechanical stimulus (e.g., a vibration or a movement) or electrical stimulus which may be recognized by a user via his tactile sensation or kinesthetic sensation. According to an embodiment, the haptic module (179) may include, for example, a motor, a piezoelectric element, or an electric stimulator.

The camera module (180) may capture a still image or moving images. According to an embodiment, the camera module (180) may include one or more lenses, image sensors, image signal processors, or flashes.

The power management module (188) may manage power supplied to the electronic device (101). According to one embodiment, the power management module (188) may be implemented as at least part of, for example, a power management integrated circuit (PMIC).

The battery (189) may supply power to at least one component of the electronic device (101). According to an embodiment, the battery (189) may include, for example, a primary cell which is not rechargeable, a secondary cell which is rechargeable, or a fuel cell.

The communication module (190) may support establishing a direct (e.g., wired) communication channel or a wireless communication channel between the electronic device (101) and the external electronic device (e.g., the electronic device (102), the electronic device (104), or the server (108)) and performing communication via the established communication channel. The communication module (190) may include one or more communication processors that are operable independently from the processor (120) (e.g., the application processor (AP)) and supports a direct (e.g., wired) communication or a wireless communication. According to an embodiment, the communication module (190) may include a wireless communication module (192) (e.g., a cellular communication module, a short-range wireless communication module, or a global navigation satellite system (GNSS) communication module) or a wired communication module (194) (e.g., a local area network (LAN) communication module or a power line communication (PLC) module). A corresponding one of these communication modules may communicate with the external electronic device via the first network (198) (e.g., a short-range communication network, such as Bluetooth™, wireless-fidelity (Wi-Fi) direct, or infrared data association (IrDA)) or the second network (199) (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module (192) may identify and authenticate the electronic device (101) in a communication network, such as the first network (198) or the second network (199), using subscriber information (e.g., international mobile subscriber identity (IMSI)) stored in the subscriber identification module (196).

The antenna module (197) may transmit or receive a signal or power to or from the outside (e.g., the external electronic device) of the electronic device (101). According to an embodiment, the antenna module (197) may include a plurality of antennas. In such a case, at least one antenna appropriate for a communication scheme used in the communication network, such as the first network (198) or the second network (199), may be selected, for example, by the communication module (190) (e.g., the wireless communication module (192)) from the plurality of antennas. The signal or the power may then be transmitted or received between the communication module (190) and the external electronic device via the selected at least one antenna.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device (101) and the external electronic device (104) via the server (108) coupled with the second network (199). Each of the electronic devices (102) and (104) may be a device of a same type as, or a different type, from the electronic device (101). According to an embodiment, all or some of operations to be executed at the electronic device (101) may be executed at one or more of the external electronic devices (102), (104), or (108). For example, if the electronic device (101) should perform a function or a service automatically, or in response to a request from a user or another device, the electronic device (101), instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device (101). The electronic device (101) may provide the outcome, with or without further processing of the outcome, as at least part of a reply to the request. To that end, a cloud computing, distributed computing, or client-server computing technology may be used, for example.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases.

As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program (140)) including one or more instructions that are stored in a storage medium (e.g., internal memory (136) or external memory (138)) that is readable by a machine (e.g., the electronic device (101)). For example, a processor (e.g., the processor (120)) of the machine (e.g., the electronic device (101)) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

Figure 2A:
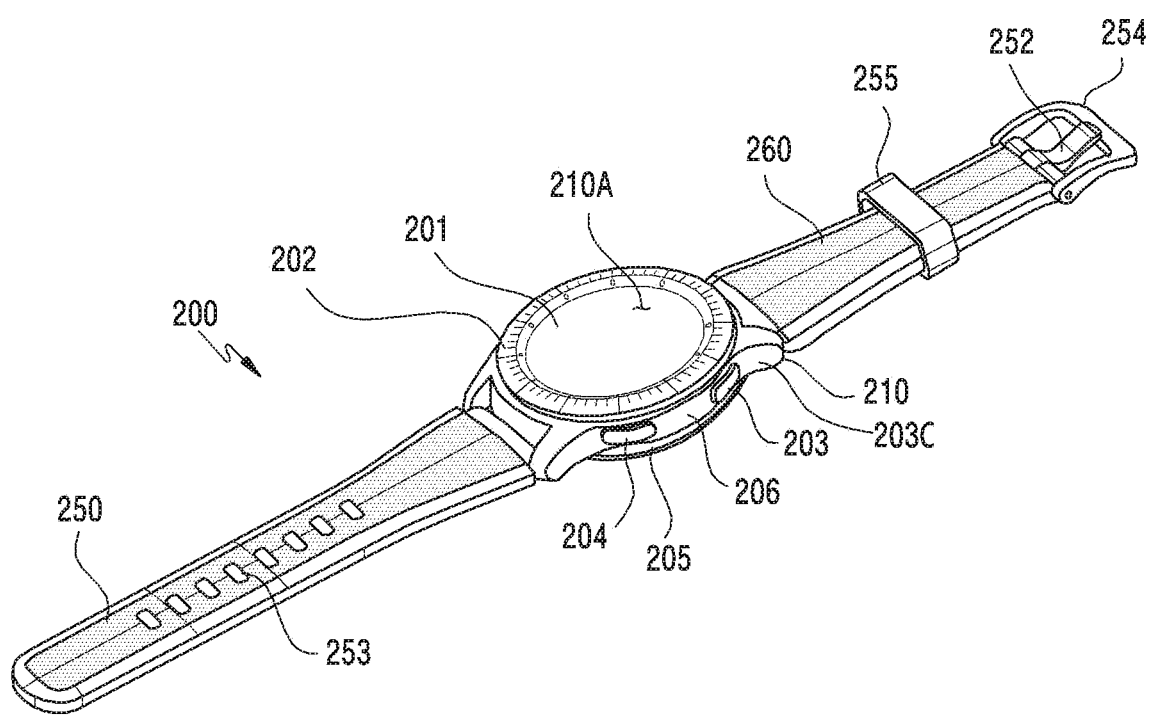
FIG. 2A is a front perspective view of a mobile electronic device according to an embodiment of the disclosure.

FIG. 2A is a front perspective view of a mobile electronic device 200 according to an embodiment of the disclosure.

Figure 2B:
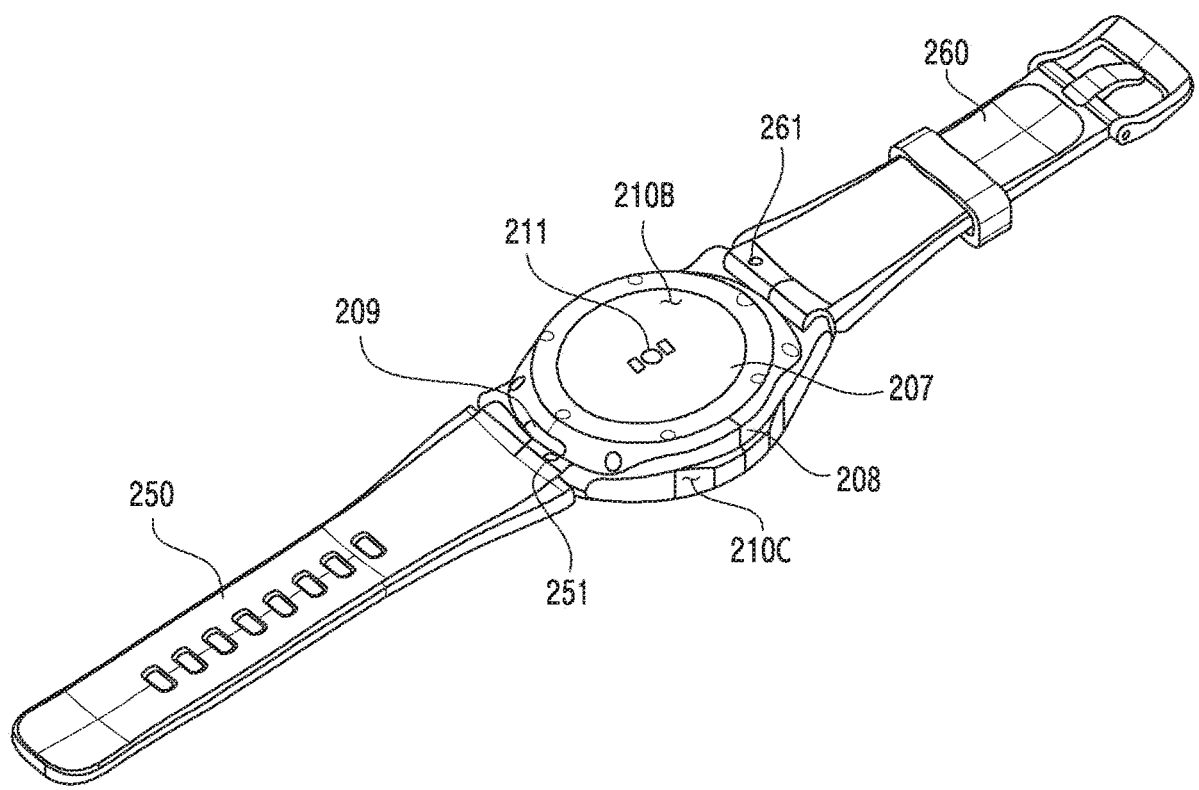
FIG. 2B is a rear perspective view of the electronic device of FIG. 2A according to an embodiment of the disclosure.

FIG. 2B is a rear perspective view of the electronic device 200 of FIG. 2A according to an embodiment of the disclosure. The electronic device 200 of FIGS. 2A and 2B may correspond to the electronic device 101 of FIG. 1.

Referring to FIGS. 2A and 2B, the electronic device 200 according to various embodiments may include a housing 210 which includes a first surface (or a front surface) 210A, a second surface (or a rear surface) 210B, and a side surface 210C which encloses a space between the first surface 210A and the second surface 210B, and fastening members 250 and 260 coupled to at least part of the housing 210 and configured to detachably fasten the electronic device 200 to a user's body part (e.g., a wrist, an ankle, etc.). In another embodiment (not shown), the housing may indicate a structure which forms part of the first surface 210A, the second surface 210B, and the side surface 210C of FIG. 2A. According to one embodiment, the first surface 210A may be formed with a front plate 201 (e.g., a glass plate including various coating layers, or a polymer plate) of which at least part is substantially transparent. The second surface 210B may be formed with a rear plate 207 which is substantially opaque. The rear plate 207 may be formed with, for example, a coated or colored glass, a ceramic, a polymer, a metal (e.g., aluminum, stainless steel (STS), or magnesium), or a combination of at least two of them. The side surface 210C may be coupled with the front plate 201 and the rear plate 207, and may be formed by a side bezel structure (or a side member) 206 including a metal and/or a polymer. In an embodiment, the rear plate 207 and the side bezel structure 206 may be integrated and include the same material (e.g., a metallic material such as aluminum). The fastening members 250 and 260 may be formed with various materials and in various shapes. An integral unit link or a plurality of unit links may be formed to move using fabrics, leather, rubber, urethane, metal, ceramic, or a combination of at least two of them.

According to an embodiment, the electronic device 200 may include at least one or more of a display 220 (see FIG. 3), audio modules 205 and 208, a sensor module 211, key input devices 202, 203, and 204, and a connector hole 209. In an embodiment, the electronic device 200 may omit at least one (e.g., the key input devices 202, 203, and 204, the connector hole 209, or the sensor module 211) of the components or further include other component(s).

The display 220 may be, for example, exposed through most of the front plate 201. A shape of the display 220 may correspond to a shape of the front plate 201, and may be in various shapes such as circular, oval, or polygonal shape. The display 220 may be coupled with or disposed close to a touch detecting circuit, a pressure sensor for measuring intensity (pressure) of a touch, and/or a fingerprint sensor.

The audio modules 205 and 208 may include a microphone hole 205 and a speaker hole 208. The microphone hole 205 may receive a microphone for acquiring external sound therein, and may receive a plurality of microphones for detecting a sound direction in an embodiment. The speaker hole 208 may be used as an external speaker or a call receiver. In an embodiment, the speaker hole 208 and the microphone hole 205 may be implemented as a single hole, or a speaker (e.g., a piezoelectric speaker) may be included without the speaker hole 208.

The sensor module 211 may generate an electric signal or a data value corresponding to an internal operating state or an external environment state of the electronic device 200. The sensor module 211 may include, for example, a biometric sensor module 211 (e.g., a heart rate monitor (HRM) sensor, an electrode sensor) disposed in the second surface 210B of the housing 210. The electronic device 200 may further include a sensor module which is not shown, for example, at least one of a gesture sensor, a gyro sensor, an atmospheric pressure sensor, a magnetic sensor, an acceleration sensor, a grip sensor, a color sensor, an infrared (IR) sensor, a biometric sensor, a temperature sensor, a humidity sensor, or an illuminance sensor.

The key input devices 202, 203, and 204 may include a wheel key 202 disposed in the first surface 210A of the housing 210 and rotating in at least one direction, and/or side keys 202 and 203 disposed in the side surface 210C of the housing 210. A shape of the wheel key 202 may correspond to the shape of the front plate 201. In another embodiment, the electronic device 200 may not include some or all of the key input devices 202, 203, and 204, and the key input devices 202, 203, and 204 not included may be implemented in a different type, such as a soft key, on the display 220.

The connector hole 209 may include another connector hole (not shown) which receives a connector (e.g., a USB connector) for transmitting and receiving power and/or data to and from an external electronic device and receives a connector for transmitting and receiving an audio signal to and from an external electronic device. The electronic device 200 may further include, for example, a connector cover (not shown) for covering at least part of the connector hole 209 and blocking an external foreign substance from entering the connector hole 209.

The fastening members 250 and 260 may be detachably fastened to at least part of the housing 210 using locking members 251 and 261. The fastening members 250 and 260 may include one or more of a fixing member 252, a fixing member coupling hole 253, a band guide member 254, and a band fixing ring 255.

The fixing member 252 may be configured to fix the housing 210 and the fastening members 250 and 260 to a user's body part (e.g., a wrist, an ankle, etc.). The fixing member coupling hole 253 may secure the housing 210 and the fastening members 250 and 260 to the user's body part in response to the fixing member 252. The band guide member 254 may be configured to limit a moving range of the fixing member 252 if the fixing member 252 is coupled with the fixing member coupling hole 253, thus closely fastening the fastening members 250 and 260 to the user's body part. The band fixing ring 255 may limit a moving range of the fastening members 250 and 260 if the fixing member 252 and the fixing member coupling hole 253 are coupled.

Figure 3:
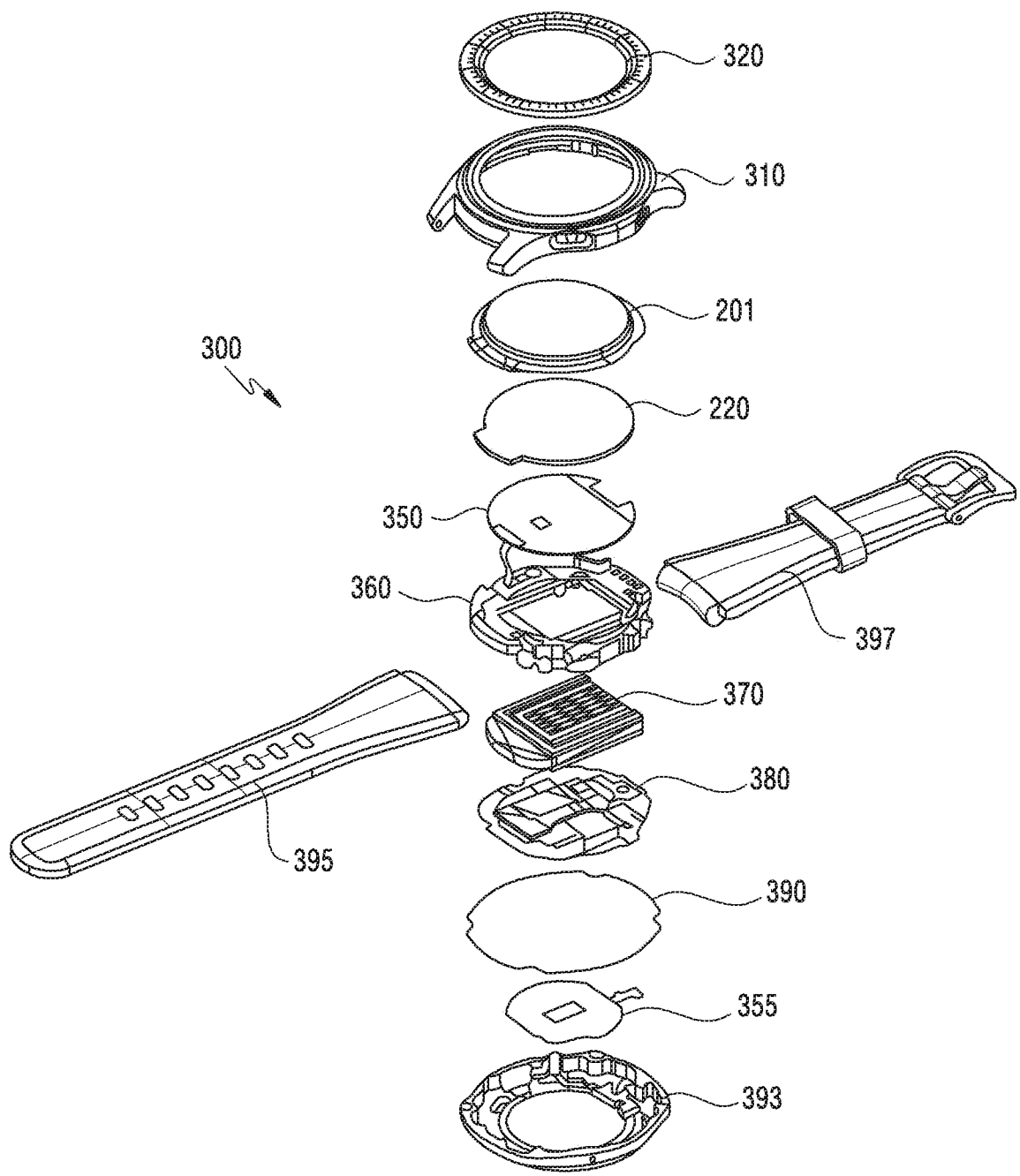
FIG. 3 is an exploded view of an electronic device of FIG. 2A according to an embodiment of the disclosure.

FIG. 3 is an exploded view of the electronic device 200 of FIG. 2A according to an embodiment of the disclosure.

Referring to FIG. 3, an electronic device 300 may include a side bezel structure 310, a wheel key 320, the front plate 201, the display 220, a first antenna 350, a second antenna 355, a support member 360 (e.g., a bracket), a battery 370, a printed circuit board 380, a sealing member 390, a rear plate 393, and fastening members 395 and 397. At least one of the components of the electronic device 300 may be identical to or similar to at least one of the components of the electronic device 200 of FIG. 2A or FIG. 2B, and their redundant descriptions shall be omitted hereafter. The support member 360 may be disposed inside the electronic device 300 and connected with the side bezel structure 310, or may be integrally formed with the side bezel structure 310. The support member 360 may be formed with, for example, a metallic material and/or a nonmetallic (e.g., polymer) material. The support member 360 may be coupled with the display 220 on one surface and coupled with the printed circuit board 380 on the other surface. The printed circuit board 380 may include a processor, a memory, and/or an interface. The processor may include one or more of, for example, a central processing unit, an application processor, a graphics processing unit (GPU), an application processor sensor processor, or a communication processor.

The memory may include, for example, a volatile memory or a nonvolatile memory. The interface may include, for example, a HDMI interface, a USB interface, an SD card interface, and/or an audio interface. The interface may electrically or physically interconnect, for example, the electronic device 300 and the external electronic device, and may include a USB connector, an SD card/multimedia card (MMC) connector, or an audio connector.

The battery 370 is a device for supplying power to at least one component of the electronic device 300, and may include, for example, a primary cell which is not rechargeable, a secondary cell which is rechargeable, or a fuel cell. At least part of the battery 370 may be disposed on substantially the same plane as, for example, the printed circuit board 380. The battery 370 may be disposed integrally within the electronic device 200, or may be detached from the electronic device 200.

The first antenna 350 may be interposed between the display 220 and the support member 360. The first antenna 350 may include, for example, a near field communication (NFC) antenna, a wireless charging antenna, and/or a magnetic secure transmission (MST) antenna. The first antenna 350 may, for example, short-range communicate with an external device or wirelessly transmit and receive the power required for charging, and transmit a short-range communication signal or a magnetic-based signal including payment data. In another embodiment, the antenna structure may be formed by part or a combination of the side bezel structure 310 and/or the support member 360.

The second antenna 355 may be interposed between the printed circuit board 380 and the rear plate 393. The second antenna 355 may include, for example, an NFC antenna, a wireless charging antenna, and/or an MST antenna. The second antenna 355 may, for example, short-range communicate with an external device or wirelessly transmit and receive the power required for charging, and transmit a short-range communication signal or a magnetic-based signal including payment data. In another embodiment, the antenna structure may be formed by part or a combination of the side bezel structure 310 and/or the rear plate 393.

The sealing member 390 may be interposed between the side bezel structure 310 and the rear plate 393. The sealing member 390 may be configured to block humidity or foreign substances from entering a space enclosed by the side bezel structure 310 and the rear plate 393.

In various embodiments, some of the components of FIGS. 2A, 2B, and 3 may correspond to some of the components of FIG. 1. For example, the display 220 may correspond to the display device 160, the audio modules 205 and 208 may correspond to the audio module 170, the sensor module 211 may correspond to the sensor module 176, the key input devices 202, 203, and 204 may correspond to the input device 150, and the battery 370 may correspond to the battery 189.

Figure 4:
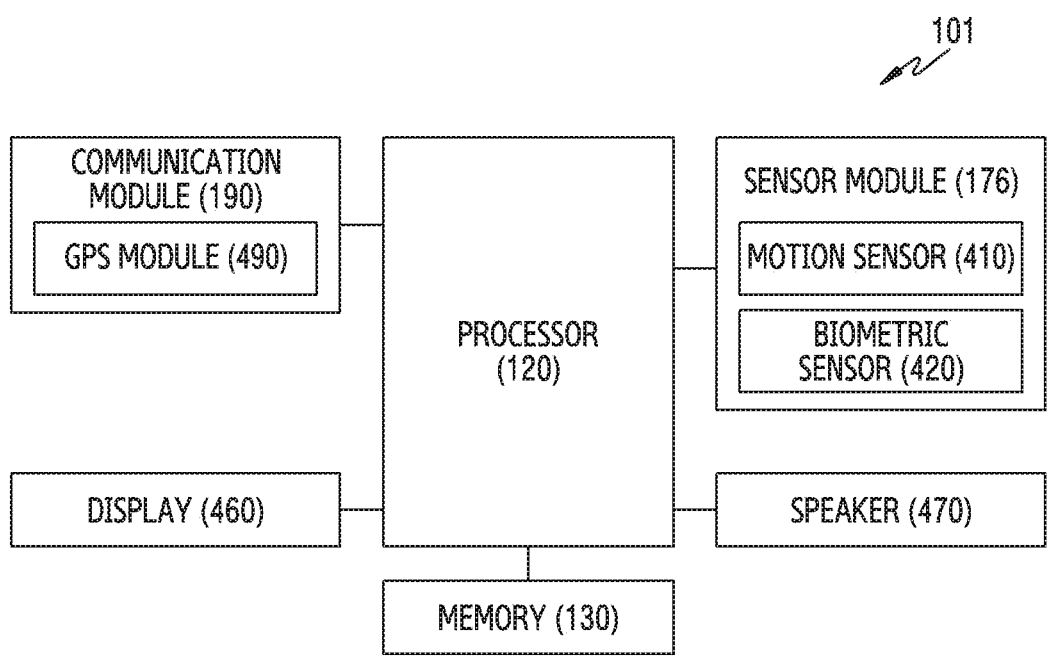
FIG. 4 illustrates an example of a functional configuration of an electronic device according to an embodiment of the disclosure.

FIG. 4 illustrates an example of a functional configuration of an electronic device 101 according to an embodiment of the disclosure. The electronic device 101 may embrace various wearable devices (e.g., a smart watch). The electronic device 101 may correspond to, for example, the electronic device 200 of FIG. 2A.

Referring to FIG. 4, the electronic device 101 may include, but not limited to, a sensor module 176, a communication module 190, a display 460, a speaker 470, a processor 120, and a memory 130. The electronic device 101 may omit at least one of the components, or add one or more other components.

The sensor module 176 may include a motion sensor 410 and a biometric sensor 420. The sensor module 176 may correspond to the sensor module 211 of FIG. 2A.

The motion sensor 410 may sense (or acquire) various signals or data, to detect a user's operating state of the electronic device 101. The motion sensor 410 may include at least one of, for example, an acceleration sensor (e.g., an accelerometer), a gyro sensor (e.g., a gyroscope), an atmospheric pressure sensor (e.g., a barometer), or a geomagnetic sensor. Data acquired using at least one of the acceleration sensor, the gyro sensor, the atmospheric pressure sensor, or the geomagnetic sensor may be used to detect the operating state of the user who wears or is equipped with the electronic device 101. The user's operating state may be classified in various manners. For example, the user's operating state may include a stationary state, a sedentary state (i.e., little activity is detected), and a moving state. The stationary state and the sedentary state may include, for example, a lying state, a sitting state, and a standing state. The moving state may include, for example, a walking state and a running state.

According to various embodiments, the motion sensor 410 may detect a direction of gravity affecting the electronic device 101, using the acceleration sensor. The motion sensor 410 may detect a change of altitude of the electronic device 101, using the atmospheric pressure sensor. The motion sensor 410 may detect a motion or a moving trajectory of the electronic device 101, using the gyro sensor. The motion sensor 410 may detect the user operating state of the electronic device 101 as one of the lying state, the sitting state, the standing state, the walking state, and the running state, using the detection results.

The biometric sensor 420 may sense or acquire a biometric signal of the user who wears or is equipped with the electronic device 101. The biometric sensor 420 may include, for example, a photoplethysmogram (PPG) sensor. The PPG sensor may measure blood volume changes in user's vessels, by measuring the amount of light from the user's body using an optical sensor. The PPG sensor may include one or more emitters and one or more receivers. For example, the emitter may include a light emitting diode (LED), and the receiver may include a photodiode (PD). The LED may convert electric energy to light energy, and the PD may convert light energy to electric energy. The LED may emit the light of one or more wavelengths. For example, the LED may emit IR and visible lights (red, blue, green). If the light emitted from the LED illuminates the user's skin of the electronic device 101, some of the light may be absorbed by the skin and other some may be reflected. The PD may detect the light reflected from the user's skin.

If the user wears or is equipped with the electronic device 101, the PPG sensor including the PD and the LED may contact the user's skin (e.g., a wrist, a finger, etc.). If the heart contracts, the blood volume increases in the vessels and the amount of the light detected by the PD may reduce. If the heart relaxes, the blood volume decreases in the vessels and the amount of the light detected by the PD may increase. Thus, the PPG sensor may acquire an AC component. In so doing, there may be no signal change (DC) in the skin or veins of the user. The AC signal acquired by the PPG sensor may be used to estimate user's blood pressure, blood sugar, heart rate, blood volume, or a combination thereof. For example, the PPG sensor may estimate the user's blood pressure, blood sugar, heart rate, or blood volume, by processing the AC signal.

The biometric sensor 420 may include, but not limited to, a laser diode (LD) or an image sensor.

The communication module 190 may establish a communication link between the electronic device 101 and the external electronic device, and perform communication via the established communication link. For example, the communication module 190 may exchange command or data with other electronic device, using global positioning system (GPS), Bluetooth, Bluetooth low energy (BLE), Wi-Fi, NFC, and so on. The communication module 190 may include, for example, a GPS module 490. The GPS module 490 may measure a current location of the electronic device 101, based on a radio signal received or detected. The GPS module 490 may be used to identify the current location (e.g., indoor, outdoor, exercise place, etc.) which may affect the user's state.

The communication module 190 may transmit information to the external electronic device (e.g., an electronic device of another user). For example, if hypotension occurs to the user of the electronic device 101, the communication module 190 may transmit (e.g., send a message or make a call) information notifying the user's hypotension to an external electronic device (e.g., an electronic device of a user's family member), based on data (e.g., contacts) stored in the electronic device 101.

The display 460 may display information. The display 460 may correspond to the display device 160 of FIG. 1 or the display 220 of FIG. 3. The display 460 may display a notification informing that the hypotension of the user of the electronic device 101 is predicted, or a notification informing that the hypotension occurs to the user of the electronic device 101.

The speaker 470 may output sound. The speaker 470 may output a designated audio signal received from the processor 120 (or the audio module 270). The speaker 470 may output a sound informing that the hypotension of the user of the electronic device 101 is predicted, or a sound informing that the hypotension occurs to the user of the electronic device 101. The sound may include a voice or a warning sound.

The processor 120 may control operations of the electronic device 101. The processor 120 may receive commands of other components (e.g., the sensor module 176, the communication module 190, the memory 130, etc.), interpret the received command, and process calculation or data according to the interpreted command. The processor 120 may be implemented in software, in hardware such as chip or circuitry, or in a combination of software and hardware. The processor 120 may include a single processor or a set of processors.

The memory 130 may indicate one or more memory sets. The memory 130 may execute instructions stored therein, based on signaling with the processor 120. The memory 130 may store data and/or command received from or generated by other components (e.g., the processor 120, the sensor module 176, the communication module 190, the display 460, etc.).

In various embodiments, the processor 120 may monitor the user's operating state of the electronic device 101 using the motion sensor 410. The processor 120 may identify the operating state of the user wearing the electronic device 101 as one of the operations states including, but not limited to, the lying state, the sitting state, the standing state, the walking state, and the running state, using the data obtained from the motion sensor 410. For example, the user's operating state may include a transition state from one of the above-stated states to another state.

To monitor the user's operating state, the processor 120 may periodically acquire sensor values from one or more sensors. For example, even if the main processor 121 is inactive (e.g., sleeping), the auxiliary processor 123 may drive with low power and periodically obtain the sensor values. Alternatively, one processor may switch between a normal state and a low-power state according to a situation. By monitoring the sensor values periodically acquired, the processor 120 may track the change in the user's operating state based on time.

The processor 120 may monitor the user's operating state using the motion sensor 410 and concurrently acquire a user's biometric signal using the biometric sensor 420 on a periodic basis. The processor 120 may monitor the user's biometric state such as blood pressure, heart rate, body temperature, perspiration quantity, blood volume, and blood sugar using the biometric sensor 420 (e.g., PPG).

The processor 120 may acquire (or model) a hypotension occurrence prediction model of the user of the electronic device 101, using first data obtained from the motion sensor 410 and second data obtained from the biometric sensor 420. For example, if the user stands up from a long-time lying position, orthostatic hypotension may occur. In addition, after an exercise, muscles relax, the body temperature rises, the blood vessels widen, and accordingly the user may suffer the hypotension. When and how the orthostatic hypotension occurs, and when and how the hypotension occurs after the exercise may differ on the user basis. For example, a person may experience the orthostatic hypotension in standing up from a 5-minute lying position, whereas another person may experience the orthostatic hypotension in standing up from a 30-minute lying position. For example, a person may experience the orthostatic hypotension after 10 minutes from standing up from the 5-minute lying position, whereas another person may experience the orthostatic hypotension after 3 minutes from standing up from the 5-minute lying position. That is, the trend of the orthostatic hypotension occurrence may differ depending on physical characteristics of the user.

Hence, by monitoring the change of the user's operating state using the motion sensor 410 and monitoring the user's operating state (e.g., blood pressure) using the biometric sensor 420, the processor 120 may acquire (e.g., model) the hypotension occurrence prediction model of the user of the electronic device 101. For example, to model the hypotension occurrence prediction model, the processor 120 may collect data regarding the user's blood pressure or heart rate range in the same posture (or operating state). To model the hypotension occurrence prediction model, the processor 120 may collect data regarding how long the user was lying before standing up to experience the orthostatic hypotension. The hypotension occurrence prediction model may be changed (e.g., updated) as the user uses the electronic device 101.

To acquire the hypotension occurrence prediction model of the user, the processor 120 may acquire user's profile information. The user's profile information may include user's gender, age, height, weight, muscle mass, body temperature, pregnancy, medication, and so on. To increase accuracy of the user's hypotension occurrence prediction model, the processor 120 may use the user's profile information. For example, the orthostatic hypotension may increase more in women than man, with age, with height, with lower muscle mass of a lower body, with pregnancy, or with a medication which widens the vessels (e.g., hypertensive medications). The processor 120 may use at least part of the user's profile information as a parameter or a factor for acquiring the hypotension occurrence prediction model.

The processor 120 may predict the user's hypotension of the electronic device 101, or determine (or identify) the occurrence of the hypotension. Based at least on the first data obtained from the motion sensor 410, the processor 120 may predict the user's hypotension by comparing with the obtained hypotension occurrence prediction model. Based at least on both of the first data obtained from the motion sensor 410 and the second data obtained from the biometric sensor 420, the processor 120 may predict the user's hypotension by comparing with the obtained hypotension occurrence prediction model. Based at least on the second data (e.g., blood pressure data) obtained from the biometric sensor 420, the processor 120 may determine (or identify) the user's hypotension.

The processor 120 may change a measurement cycle of the first data using the motion sensor 410 and/or a measurement cycle of the second data using the biometric sensor 420, according to the user's operating state. In various embodiments, the processor 120 may identify a timing at which the hypotension is highly likely to occur to the user, based on monitoring the user's operating state using the motion sensor 410. For example, the processor 120 may start acquiring the second data using the biometric sensor 420 from the timing at which the hypotension is highly likely to occur to the user. For example, the processor 120 may increase the measurement cycle of the second data using the biometric sensor 420 from the timing at which the hypotension is highly likely to occur to the user. The timing at which the hypotension is highly likely to occur to the user may be, for example, a timing at which the user stands up from the lying position or the user ends his/her exercise.

Figure 5:
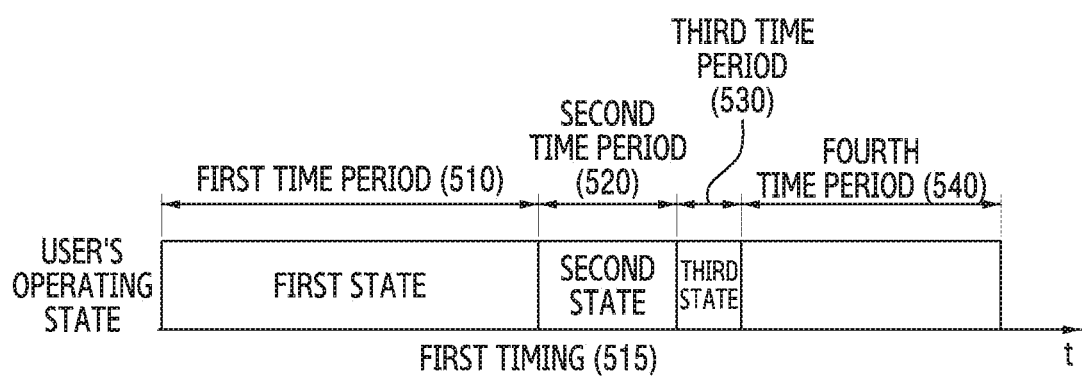
FIG. 5 illustrates an example of operating state changes identified at an electronic device according to an embodiment of the disclosure.

FIG. 5 illustrates an example of operating state changes identified at an electronic device according to an embodiment of the disclosure.

Referring to FIG. 5, the processor 120 may detect that the user's operating state stays in a first state, in a first time period 510. For example, in case of the orthostatic hypotension, the first state may be the lying state or the sitting state. For example, in case of the hypotension after exercise, the first state may be an exercise state (e.g., the walking state, the running state, etc.). According to an embodiment, in the first time period 510 of the first state maintained, the biometric sensor 420 may be disabled and only the motion sensor 410 may be enabled. According to another embodiment, in the first time period 510 of the first state maintained, the biometric sensor 420 may monitor the user's biometric state (e.g., blood pressure, heart rate, body temperature, perspiration quantity, blood volume, and blood sugar) on a low cycle. In one embodiment, if the user's operating state is the exercise state in the first time period 510, the processor 120 may further monitor calorie consumption or dehydration rate.

Using the first data obtained from the motion sensor 410, the processor 120 may detect that the user's operating state starts to change at a first timing 515. The processor 120 may detect a second state in which the user's operating state changes in a second time period 520. That is, the second state may indicate that the user's operating state transits from one state to another state. For example, in case of the orthostatic hypotension, the second state may indicate the transition from the lying state to the sitting state or the transition from the sitting state to the standing state. In the orthostatic hypotension, the second state may indicate a two-step transition from the lying state to the sitting state and from the sitting state to the standing state. For example, in the hypotension after the exercise, the second state may indicate the transition from the walking state to the standing state or to the sitting state. In the hypotension after the exercise, the second state may indicate the transition from the running state to the walking state, the standing state, or the sitting state.

At the first timing 515 which is the transition to the second state, the hypotension may increase to the user. Hence, the processor 120 may enable the biometric sensor 420, from the first timing 515 which is the transition to the second state. Alternatively, the processor 120 may increase the measurement cycle of the biometric sensor 420, from the first timing 515 which is the transition to the second state. For example, the measurement cycle of the biometric sensor 420 may be a first cycle in the first time period 515, and may be a second cycle which higher than the first cycle from the first timing 515 (e.g., in the second time period 520). In one embodiment, the processor 120 may also increase the measurement cycle of the motion sensor 410 from the first timing 515.

Using the first data obtained from the motion sensor 410 in a third time period 530, the processor 120 may identify (or determine) the user's operating state as a third state. The processor 120 may confirm the user's operating state as the third state, based on identifying that the user's operating state stays in the third state in the third time period 530. That is, the third time period 530 may be the time for confirming the user's operating state to any one state. For example, in the orthostatic hypotension, the processor 120 may confirm the user's standing state or sitting state, based on identifying that the standing state or sitting state maintains in the third time period 530. For example, in the hypotension after the exercise, the processor 120 may confirm that the user terminates the exercise, based on identifying that the walking state, the standing status, or the sitting state maintains in the third time period 530. The third time period 530 (e.g., 3 seconds) for confirming the user's operating state in response to the orthostatic hypotension may be different from the third time period 530 (e.g., 30 minutes) for confirming the user's operating state in response to the hypotension after the exercise. Hence, based on the first data obtained from the motion sensor 410 in the first time period 510 and the second time period 520, the processor 120 may set the third time period 530 for confirming the user's operating state. For example, if detecting that the user stands up from lying or sitting in the first time period 510 and the second time period 520, the processor 120 may set the third time period 530 to three seconds to determine that the user fully stands up. For example, if detecting that the user stops exercising in the first time period 510 and the second time period 520, the processor 120 may set the third time period 530 to 30 minutes to determine that the user completely terminates the exercise. Since the hypotension is highly likely to occur to the user even in the third time period 530, the measurement cycle of the biometric sensor 420 may be the second cycle which is higher than the first cycle, or a third cycle which is higher than the second cycle.

If the user's operating state is confirmed to the third state, since the hypotension is highly likely to occur to the user in a next fourth time period 540, continuous monitoring may be required. A length of the fourth time period 540 requiring the continuous monitoring may vary depending on the orthostatic hypotension or the hypotension after the exercise. For example, the length of the fourth time period 540 for the orthostatic hypotension may range from 30 seconds to 1 minute, and the length of the fourth time period 540 for the hypotension after the exercise may range from 90 minutes to 120 minutes. Alternatively, the length of the fourth time period 540 requiring the continuous monitoring may differ per user. Thus, the processor 120 may set the length of the fourth time period 540, based on the hypotension occurrence prediction model of the user. Since the hypotension is highly likely to occur to the user in the fourth time period 540, the measurement cycle of the biometric sensor 420 may be, but not limited to, the second cycle which is higher than the first cycle, or the third cycle which is higher than the second cycle.

Although not depicted, ever after the fourth time period 540 ends, the processor 120 may further monitor the user's blood pressure using the biometric sensor 420, in a fifth time period designated. Since the hypotension is relatively less likely to occur to the user in the fifth time period, the measurement cycle of the biometric sensor 420 in the fifth time period may be the second cycle which is lower than the third cycle. Alternatively, the measurement cycle of the biometric sensor 420 in the fifth time period may be, but not limited to, between the first cycle and the second cycle. Monitoring using the biometric sensor 420 in the fifth time period may be performed if necessary or selectively.

If the hypotension does not occur to the user until the fourth time period 540 (or the fifth time period) ends, the processor 120 may release the hypotension monitoring. For example, the processor 120 may disable the biometric sensor 420, or may change the measurement cycle of the biometric sensor 420 to the first cycle which is the lowest cycle.

In the first time period 510, the second time period 520, and the third time period 530, the processor 120 may predict the hypotension of the user. For example, the processor 120 may predict the user's hypotension, by comparing the first data obtained from the motion sensor 410 with the hypotension occurrence prediction model. For example, the processor 120 may predict the user's hypotension, by comparing the first data obtained from the motion sensor 410 and the second data obtained from the biometric sensor 420 with the hypotension occurrence prediction model.

In response to predicting the user's hypotension, the processor 120 may provide a notification 610 of the user's hypotension predicted.

Figure 6:
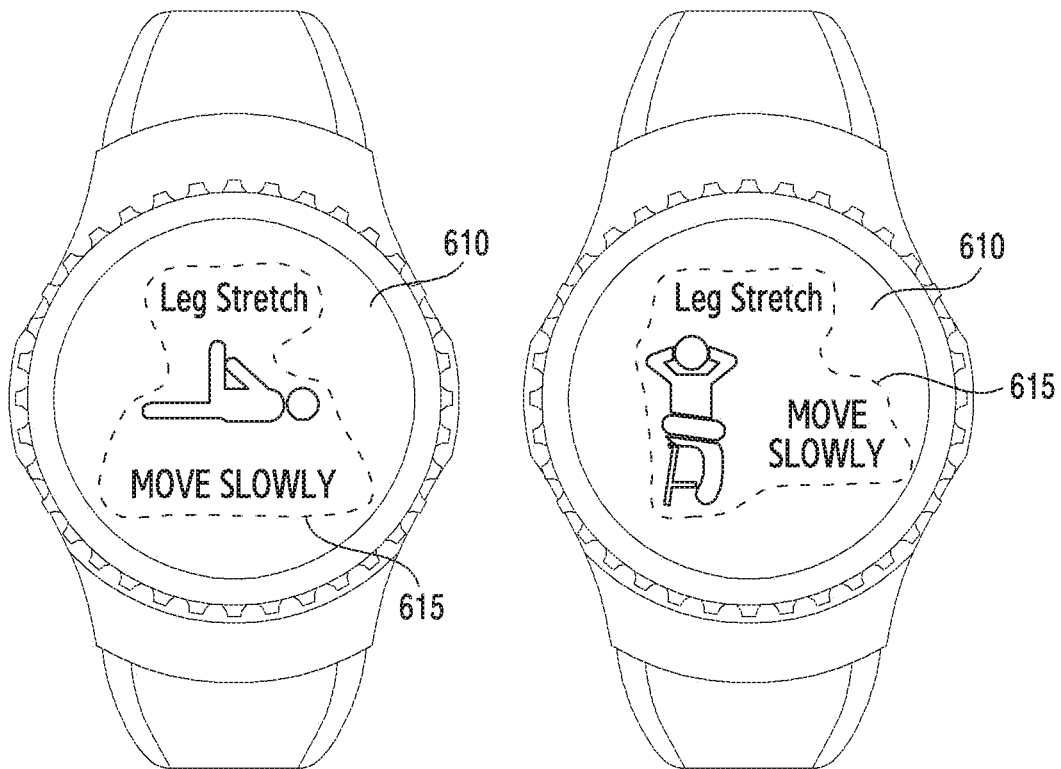
FIG. 6 illustrates an example of a notification provided at an electronic device according to an embodiment of the disclosure.

Referring to FIG. 6, the processor 120 may display the notification 610 of the user's hypotension predicted, on the display 460. The notification 610 may include a guidance 615 provided to the user, to prevent the hypotension. For example, the processor 120 may output an audio signal (e.g., voice or warning sound) of the user's hypotension predicted, through the speaker 470.

FIG. 6 illustrates the example of the notification 610 if the occurrence of the orthostatic hypotension is predicted, according to an embodiment of the disclosure.

The electronic device 101 may provide another notification including the guidance 615 and another guidance and notifying the predicted hypotension. For example, if predicting the hypotension within a specific time period from the end of the user's exercise, the processor 120 may provide another notification including another guidance which is distinguished from the guidance 615 of the notification 610.

In the second time period 520, the third time period 530, and the fourth time period 540, the processor 120 may determine the user's hypotension occurred. In the second time period 520, the third time period 530, and the fourth time period 540, the processor 120 may determine the user's hypotension occurrence, based on the second data (e.g., blood pressure data) obtained from the biometric sensor 420.

In response to identifying the user's hypotension occurrence, the processor 120 may provide information notifying the user of the hypotension.

Figure 7:
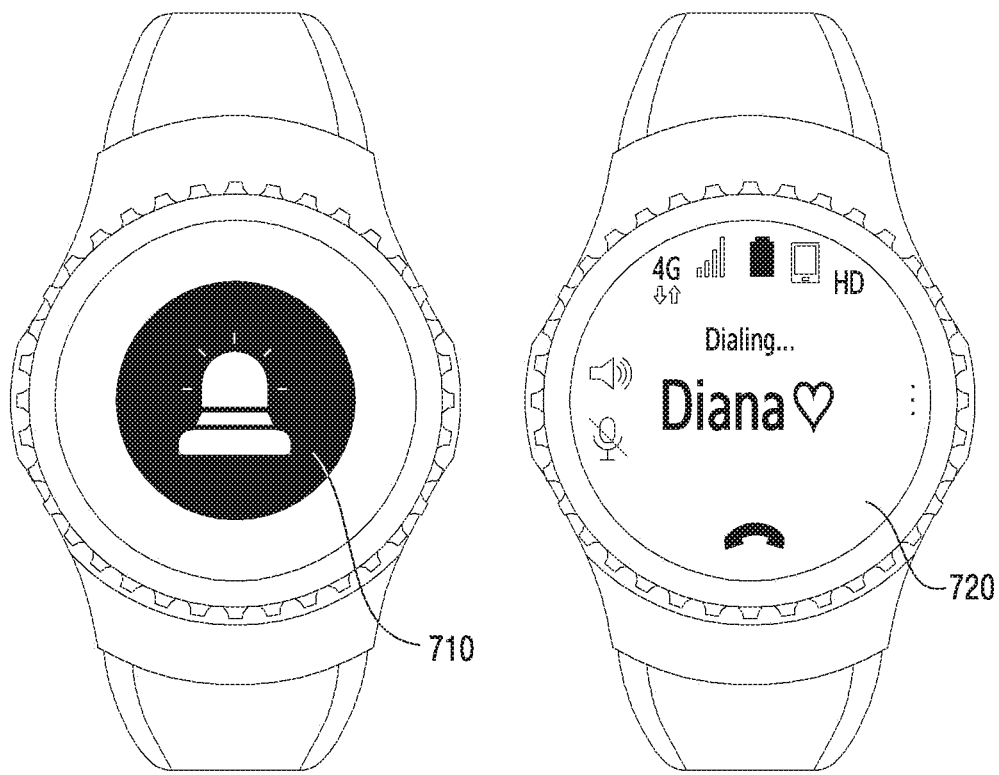
FIG. 7 illustrates another example of a notification provided at an electronic device according to an embodiment of the disclosure.

For example, as shown in FIG. 7, the processor 120 may display a warning 710 of the hypotension to the user, on the display 460. Alternatively, the processor 120 may notify the user's hypotension to user's vicinity, by outputting an audio signal (e.g., voice or warning sound) through the speaker 470. Alternatively, if the warning 710 is not released on the display 460, since the user may be in a serious danger, the processor 120 may send a message or make a call to notify the user's hypotension to other electronic device, based on designated identification information, as shown in a screen 720.

FIG. 7 illustrates the example for making a call to other electronic device based on the identification information registered by the user, according to an embodiment of the disclosure.

Referring to FIG. 7, for example, the processor 120 may make a call or send a message to other electronic device, based on default identification information (e.g., an emergency telephone number such as 911 in the United States), rather than the identification information registered by the user. After the call is made or the message is transmitted to other electronic device based on the identification information, the other electronic device receiving the call or the message may track the location of the electronic device 101 to provide an emergency service to the user. For example, the processor 120 may provide a notification to other electronic device which resides within a designated distance from the electronic device 101. In various embodiments, priorities of the other electronic device indicated by the default identification information, the other electronic device indicated by the identification information registered by the user, and the other electronic device located within the designated distance may be adjusted based on a user input.

As state above, an electronic device according to various embodiments may include a housing (e.g., the housing 210), a user interface, a PPG sensor (e.g., the biometric sensor 420) exposed through at least part of the housing, a motion sensor (e.g., the motion sensor 410) disposed in the housing, a processor (e.g., the processor 120) operatively coupled with the user interface, the PPG sensor, and the motion sensor, and a memory (e.g., the memory 130) operatively coupled with the processor, wherein the memory may store instructions, when executed, causing the processor to, if first data from the motion sensor indicates a change of a selected pattern, identify a blood pressure value based at least in part on second data from the PPG sensor, and if the identified blood pressure value is lower than a first threshold, provide a notification through the user interface.

In various embodiments, the selected pattern may include a pattern which changes from a state in which the first data is lower than a second threshold to a state in which the first data is higher than a third threshold.

In various embodiments, the selected pattern may include a pattern which changes from a state in which the first data is than a third threshold to a state in which the first data is lower than a second threshold.

In various embodiments, the instructions may cause the processor to, before the change of the selected pattern occurs, monitor a blood pressure from the PPG sensor on a first cycle, and after the change of the selected pattern occurs, monitor the blood pressure on a second cycle which is shorter than the first cycle.

In various embodiments, the user interface may include at least one of a display, a speaker, or an LED.

In various embodiments, the instructions may cause the processor to model a hypotension occurrence prediction model of a user based on the first data and the second data. In various embodiments, the instructions may cause the processor to predict hypotension occurrence of the user, based on comparing the first data with the hypotension occurrence prediction model. In various embodiments, the instructions may cause the processor to, in response to predicting the hypotension occurrence of the user, provide a guidance for preventing the hypotension of the user, on a display of the electronic device.

In various embodiments, the hypotension occurrence prediction model may be updated according to using the electronic device.

In various embodiments, the instructions may cause the processor to, if the identified blood pressure value is lower than the first threshold, provide a notification to another electronic device using designated identification information.

Figure 8:
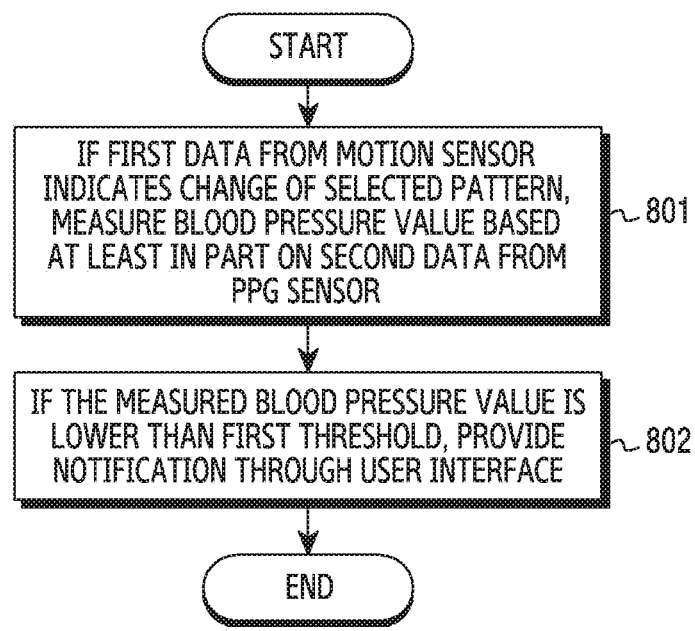
FIG. 8 illustrates an example of operations of an electronic device according to an embodiment of the disclosure.

FIG. 8 illustrates an example of operations of an electronic device 101 according to an embodiment of the disclosure.

Referring to FIG. 8, in operation 801, if the first data from the motion sensor 410 indicates a change of a selected pattern, the processor 120 may measure a blood pressure value based at least in part on the second data from the PPG sensor (e.g., the biometric sensor 420). For example, the change of the selected pattern may indicate a change of the user's operating state from the lying state to the sitting state or the standing state, or from the sitting state to the standing state. For example, the change of the selected pattern may indicate a change of the user's operating state from the exercise state (e.g., the walking state or the running state) to the standing state or the sitting state. If detecting the change of the selected pattern through the motion sensor 410, the processor 120 may enable the PPG sensor or the increase the measurement cycle of the PPG sensor. The processor 120 may identify the blood pressure value of the user, based on the second data (e.g., blood pressure data) obtained from the PPG sensor.

In operation 802, if the measured blood pressure value is lower than a first threshold, the processor 120 may provide a notification through a user interface. For example, the user interface may include at least one of the display 460, the speaker 470, or the LED. For example, the processor 120 may display the notification of the hypotension to the user on the display 460. Alternatively, the processor 120 may notify the user's hypotension to user's vicinity, by outputting an audio signal (e.g., voice or warning sound) through the speaker 470. Alternatively, if the displayed warning is not released on the display 460, since the user may be in a serious danger, the processor 120 may send a message or make a call to another designated electronic device (e.g., an electronic device of a user's family member) to notify the user's hypotension. Alternatively, the processor 120 may provide a notification to other electronic device which resides within a designated distance from the electronic device 101.

Figure 9:
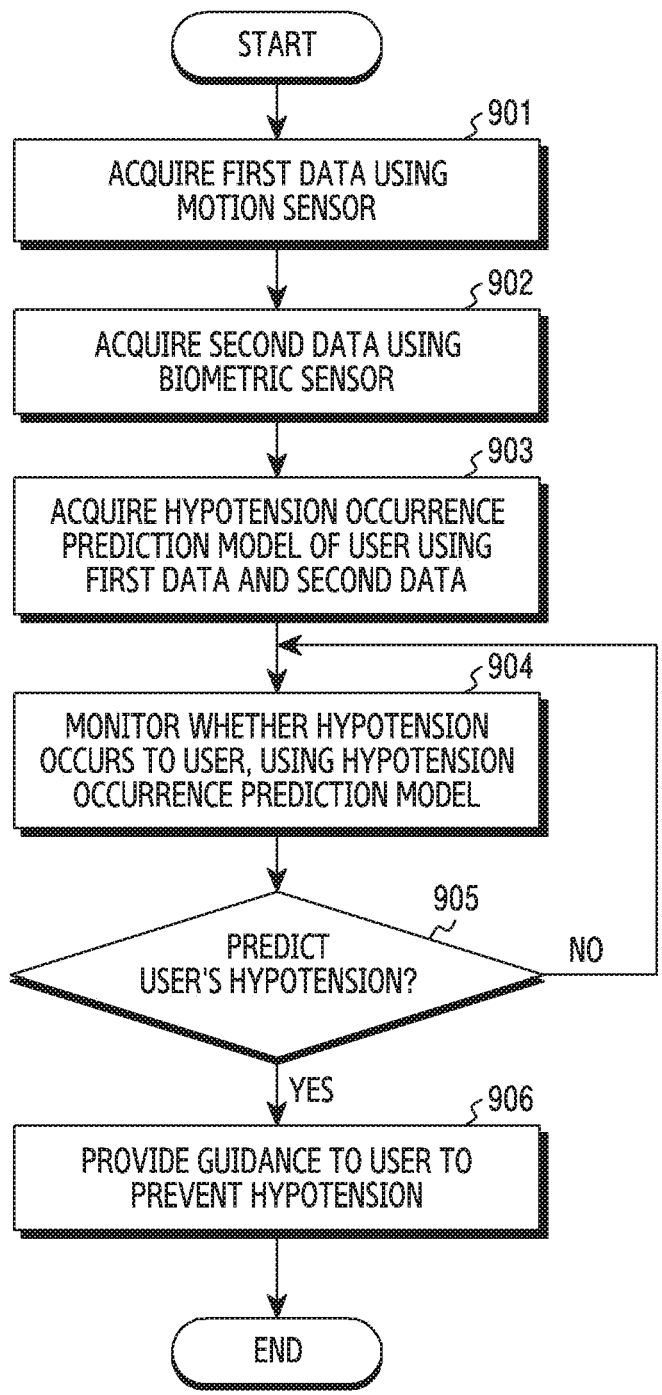
FIG. 9 illustrates another example of operations of an electronic device according to an embodiment of the disclosure.

FIG. 9 illustrates another example of operations of an electronic device 101 according to an embodiment of the disclosure.

Referring to FIG. 9, in operation 901, the processor 120 may acquire first data using the motion sensor 410. For example, the motion sensor 410 may include at least one of an acceleration sensor, a gyro sensor, an atmospheric pressure sensor, or a geomagnetic sensor. The first data acquired using the motion sensor 410 may be used to identify the user's operating state. The user's operating state may include, for example, the lying state, the sitting state, the standing state, the walking state, and/or the running state.

In operation 902, the processor 120 may acquire second data using the biometric sensor 420 (e.g., a PPG sensor). The second data may include at least one of the user's blood pressure, heart rate, body temperature, perspiration quantity, blood volume, or blood sugar.

In operation 903, the processor 120 may acquire (or model) a hypotension occurrence prediction model of the user, using the first data and the second data. For example, to model the hypotension occurrence prediction model, the processor 120 may collect data of user's blood pressure values based on a change of the first data (and/or the second data). To acquire the hypotension occurrence prediction model of the user, the processor 120 may acquire user's profile information. The user's profile information may include user's gender, age, height, weight, muscle mass, body temperature, pregnancy, medication, and so on. The processor 120 may use at least part of the user's profile information as a parameter or a factor for acquiring the hypotension occurrence prediction model.

In operation 904, the processor 120 may monitor whether hypotension occurs to the user of the electronic device 101, using the acquired hypotension occurrence prediction model. For example, the processor 120 may predict whether the hypotension occurs to the user, by comparing the first data obtained from the motion sensor 410 with the hypotension occurrence prediction model. For example, the processor 120 may predict whether the hypotension occurs to the user, by comparing the first data obtained from the motion sensor 410 and the second data obtained from the biometric sensor 420 with the hypotension occurrence prediction model.

In operation 905, if not predicting the user's hypotension, the processor 120 may repeat monitoring of operation 904. Based on predicting the user's hypotension, the processor 120 may provide a guidance to the user to prevent the hypotension in operation 906. For example, the processor 120 may display a notification of the predicted hypotension, on the display 460.

As stated above, an operating method of an electronic device may include, if first data from a motion sensor of the electronic device indicates a change of a selected pattern, identifying a blood pressure value based at least in part on a second data from a PPG sensor of the electronic device, and if the identified blood pressure value is lower than a first threshold, providing a notification through a user interface of the electronic device.

In various embodiments, the selected pattern may include a pattern which changes from a state in which the first data is lower than a second threshold to a state in which the first data is higher than a third threshold.

In various embodiments, the selected pattern may include a pattern which changes from a state in which the first data is than a third threshold to a state in which the first data is lower than a second threshold.

In various embodiments, the operating method may further include, before the change of the selected pattern occurs, monitoring a blood pressure from the PPG sensor on a first cycle, and after the change of the selected pattern occurs, monitoring the blood pressure on a second cycle which is shorter than the first cycle.

In various embodiments, the user interface may include at least one of a display, a speaker, or an LED.

In various embodiments, the operating method may further include modeling a hypotension occurrence prediction model of a user based on the first data and the second data.

In various embodiments, the operating method may further include predicting hypotension occurrence of the user, based on comparing the first data with the hypotension occurrence prediction model. In various embodiments, the operating method may further include, in response to predicting the hypotension occurrence of the user, providing a guidance for preventing the hypotension of the user, on a display of the electronic device.

In various embodiments, the hypotension occurrence prediction model may be updated according to using the electronic device.

In various embodiments, the operating method may further include, if the identified blood pressure value is lower than the first threshold, providing a notification to another electronic device using designated identification information.

An apparatus and a method according to various embodiments may provide a service for hypotension, by predicting or determining hypotension occurrence of a user of an electronic device.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. An electronic device comprising:
   a housing;
   a user interface;
   a photoplethysmogram (PPG) sensor exposed through at least part of the housing;
   a motion sensor disposed in the housing;
   at least one processor operatively coupled with the user interface, the PPG sensor, and the motion sensor; and
   a memory operatively coupled with the at least one processor,
   wherein the memory stores instructions which, when executed by the at least one processor, cause the at least one processor to:
   obtain a first data from the motion sensor with the PPG sensor disabled,
   detect a change of a user's operating state which increases a probability of occurrence of hypotension based on that the first data from the motion sensor indicates a first change of a first selected pattern,
   in response to detecting the change of the user's operating state, enable the PPG sensor during a predesignated time period to monitor a blood pressure value based at least in part on second data from the PPG sensor, and
   based on the blood pressure value being lower than a first threshold, provide a notification through the user interface, and wherein the predesignated time period is set based on a type of hypotension to be monitored and information on physical characteristics of the user.

2. The electronic device of claim 1, wherein the first selected pattern comprises a pattern which changes from a state in which the first data is lower than a second threshold to a state in which the first data is higher than a third threshold.

3. The electronic device of claim 1, wherein the first selected pattern comprises a pattern which changes from a state in which the first data is higher than a third threshold to a state in which the first data is lower than a second threshold.

4. The electronic device of claim 1, wherein the instructions further cause the at least one processor to:
before a second change of a second selected pattern occurs, control the PPG sensor to monitor a blood pressure on a first cycle; and
after the second change of the second selected pattern occurs, control the PPG sensor to monitor the blood pressure on a second cycle which is shorter than the first cycle.

5. The electronic device of claim 1, wherein the user interface comprises at least one of a display, a speaker, or a light emitting diode (LED).

6. The electronic device of claim 1, wherein the instructions further cause the at least one processor to:
based on the blood pressure value being lower than the first threshold, provide a notification to another electronic device using designated identification information.

7. The electronic device of claim 1,
wherein the user's operating state comprises at least one of a stationary state, a sedentary state, or a moving state, and
wherein the instructions further cause the at least one processor to:
when the type of hypotension to be monitored is a first type, detect that the user's operating state is changed from a first state to a second state using the first data, and
when the type of hypotension to be monitored is a second type, detect that the user's operating state is changed from a third state to a fourth state using the first data.

8. An operating method of an electronic device, the operating method comprising:
obtaining a first data from a motion sensor with a PPG sensor disabled;
detecting a change of a user's operating state which increases a probability of occurrence of hypotension based on that the first data from the motion sensor of the electronic device indicates a first change of a first selected pattern,
in response to detecting the change of the user's operating state, enabling a photoplethysmogram (PPG) sensor during a predesignated time period to monitor a blood pressure value based at least in part on a second data from the PPG sensor of the electronic device; and
based on the blood pressure value being lower than a first threshold, providing a notification through a user interface of the electronic device,
wherein the predesignated time period is set based on a type of hypotension to be monitored and information on physical characteristics of the user.

9. The operating method of claim 8, wherein the first selected pattern comprises a pattern which changes from a state in which the first data is lower than a second threshold to a state in which the first data is higher than a third threshold.

10. The operating method of claim 8, wherein the first selected pattern comprises a pattern which changes from a state in which the first data is higher than a third threshold to a state in which the first data is lower than a second threshold.

11. The operating method of claim 8, further comprising:
before a second change of a second selected pattern occurs, monitoring a blood pressure from the PPG sensor on a first cycle; and
after the second change of the second selected pattern occurs, monitoring the blood pressure from the PPG sensor on a second cycle which is shorter than the first cycle.

12. The operating method of claim 8, further comprising:
based on the blood pressure value being lower than the first threshold, providing a notification to another electronic device using designated identification information.

* * * * *